United States Patent
Sautereau

(10) Patent No.: US 11,291,813 B2
(45) Date of Patent: Apr. 5, 2022

(54) STORAGE AND DISPENSER DEVICE

(71) Applicant: BOEHRINGER INGELHEIM ANIMAL HEALTH USA INC., Duluth, GA (US)

(72) Inventor: Christophe Sautereau, Chaponost (FR)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 925 days.

(21) Appl. No.: 15/769,664

(22) PCT Filed: Oct. 21, 2016

(86) PCT No.: PCT/US2016/058010
§ 371 (c)(1),
(2) Date: Apr. 19, 2018

(87) PCT Pub. No.: WO2017/070408
PCT Pub. Date: Apr. 27, 2017

(65) Prior Publication Data
US 2018/0304061 A1    Oct. 25, 2018

Related U.S. Application Data

(60) Provisional application No. 62/244,616, filed on Oct. 21, 2015.

(51) Int. Cl.
*A61M 35/00*    (2006.01)
*A61J 1/06*    (2006.01)
*B65D 1/09*    (2006.01)
*A61M 39/00*    (2006.01)

(52) U.S. Cl.
CPC ............ *A61M 35/003* (2013.01); *A61J 1/065* (2013.01); *A61M 39/00* (2013.01); *B65D 1/09* (2013.01)

(58) Field of Classification Search
CPC ...... A61M 35/003; A61M 9/00; A61M 39/00; A61J 1/065; B65D 1/09; A47J 37/00
USPC ........................... 604/310; 141/26, 352, 357
See application file for complete search history.

(56) References Cited

U.S. PATENT DOCUMENTS

| | | | | |
|---|---|---|---|---|
| 2,418,036 | A * | 3/1947 | Lane | B65D 83/754 222/3 |
| 4,052,986 | A * | 10/1977 | Scaife | A61M 31/00 604/204 |
| 5,638,872 | A * | 6/1997 | Porter | A47J 37/106 141/26 |
| 6,394,317 | B1 * | 5/2002 | Faughey | B05B 11/3008 222/153.13 |
| 7,219,816 | B1 | 5/2007 | Xia | |
| 2004/0267182 | A1 * | 12/2004 | Davis | A61L 2/0088 604/2 |
| 2006/0054241 | A1 * | 3/2006 | Bartholomew | A61M 39/00 141/105 |
| 2009/0013993 | A1 * | 1/2009 | Bird | A61M 15/0086 128/200.15 |

(Continued)

FOREIGN PATENT DOCUMENTS

WO    98/57574 A1    12/1998

*Primary Examiner* — Andrew J Mensh
(74) *Attorney, Agent, or Firm* — Jamie Graham

(57) ABSTRACT

A storage and manual dispenser apparatus for dispensing a pharmaceutical liquid under atmospheric pressure. This apparatus retains the liquid in a controlled and stable environment during storage.

2 Claims, 18 Drawing Sheets

(56) References Cited

U.S. PATENT DOCUMENTS

2012/0211946 A1* 8/2012 Halili ..................... A61M 5/31
                                                                 277/607

* cited by examiner

B-B

A-A

A-A

B-B

C-C

STORAGE AND DISPENSER DEVICE

CROSS-REFERENCE TO RELATED APPLICATIONS

This application claims priority to U.S. provisional patent application Ser. No. 62/244,616, filed on 21 Oct. 2015, and herein incorporated by reference in its entirety.

RELATED APPLICATIONS/INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention.

FIELD OF THE INVENTION

The present invention relates to a storage and manual dispenser apparatus for dispensing a pharmaceutical liquid under atmospheric pressure. This apparatus retains the liquid in a controlled and stable environment during storage.

BACKGROUND OF THE INVENTION

Many known topical applicators use a pipette, squeeze container or syringe type applicator. When applying pharmaceutical liquids, such as pesticides, to a targeted zone on an animal's skin or coat using an applicator device, the device user faces numerous problems applying the liquid uniformly and consistently due to the animal's rapid movement or nervousness of the user in applying the liquid. Due to the inability of these devices to control the dispensing of the liquid, these problems result the full dose of liquid only being partially applied or not being applied, or not being uniformly applied in the targeted zone. Inadequate or inaccurate application of the pharmaceutical liquid can lead to less than optimal treatment of the disease Many known applicator devices fail to have an easy means to control the dispense of pharmaceutical liquid or the device does not have a mechanism to intermittently stop applying the liquid once the container is opened. Users face problems with known applicators by the user uncontrollably pushing all the pharmaceutical liquid in one instance or the device has no mechanism to intermittently stop applying the liquid once the liquid container is opened. When dispensing liquid from a device having a container with only one hole, air must enter the container through the hole at the same time as liquid must exit through the hole, so that a volume of poured liquid can be replaced with air. This results in what is commonly known as "gurgling" of the liquid being dispensed which causes the liquid to splash as it is dispensed and non-uniform distribution of the liquid.

Dispensers known in the art include those disclosed in UK patent application GB2156949, European Patent No. 0046754, US Patent Application Nos. US2008/0179763 and US2007/0189835, and U.S. Pat. No. 5,638,872. Tip applicators known in the art include those disclosed in UK patent GB1444848 and UK patent application no. GB2120630 and U.S. Pat. Nos. 7,219,816, 4,688,703, 7,810,680 and 8,272,522.

In view of the foregoing, there is a need for a storage and applicator device, including applicator devices for topical compositions, etc. that overcomes these shortcomings and may provide one or more advantageous features.

SUMMARY OF THE INVENTION

Accordingly, it is an object of the invention to provide an easy to use and cost effective device to dispense pharmaceutical liquid on a targeted zone of a patient, the device having three configurations for storage, dispensing of the liquid and intermittent stopping of dispensing of the liquid.

A further object of the invention is to provide a dispenser device, and a method of use thereof, which can be used by one hand of the user and can easily control the dispensing of the liquid by manual control of the valve on the device.

Another object of the invention is to provide a dispenser device can be controlled to dispense the liquid under gravity.

Another object of the invention is to provide a storage device to store the pharmaceutical liquid for a pharmaceutical acceptable period of time.

The invention in its particular features will become more apparent from the following detailed description considered with reference to the accompanying examples. The following description will continue to discuss the problems and solutions offered by the present invention as they pertain to veterinary applications.

It is noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is further noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

BRIEF DESCRIPTION OF THE DRAWINGS

For the purposes of illustrating the invention, there is shown in the drawings various forms which are presently disclosed. However, it being understood that this invention is not limited to the precise arrangements and instrumentalities particularly shown.

DETAILED DESCRIPTION OF THE INVENTION

Figure 1A:
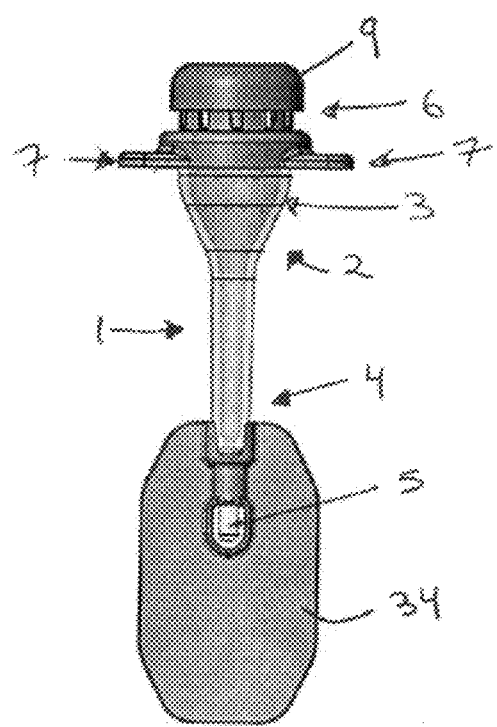
FIG. 1A is a front view of a device according to the invention.
Figure 1B:
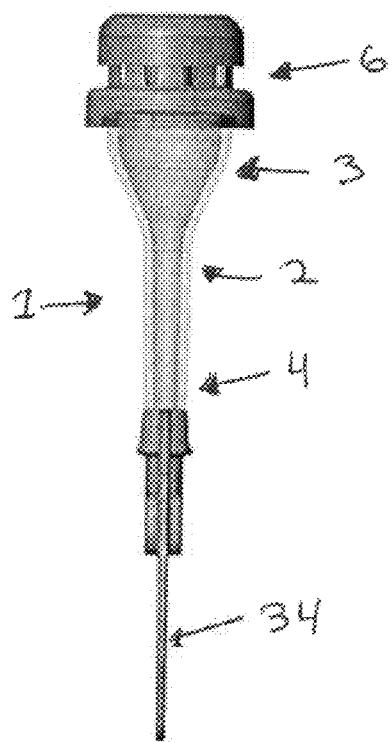
FIG. 1B is a side view of a device according to the invention.

FIG. 1A is a front view, and FIG. 1B, is a side view illustrating the device of the present invention in the storage position. A device (1) for storing and dispensing a topical pharmaceutical liquid having a substantially rigid elongated container (2), configured to hold the liquid therein, having a proximal end (3) and a distal end (4) with respective openings and the distal end of the container tapering into an applicator tip, the distal opening being closed by a closure means (5) having lugs (34), the device also have an air valve (6), peripheral flanges (7) and cap (9).

Figure 2A:
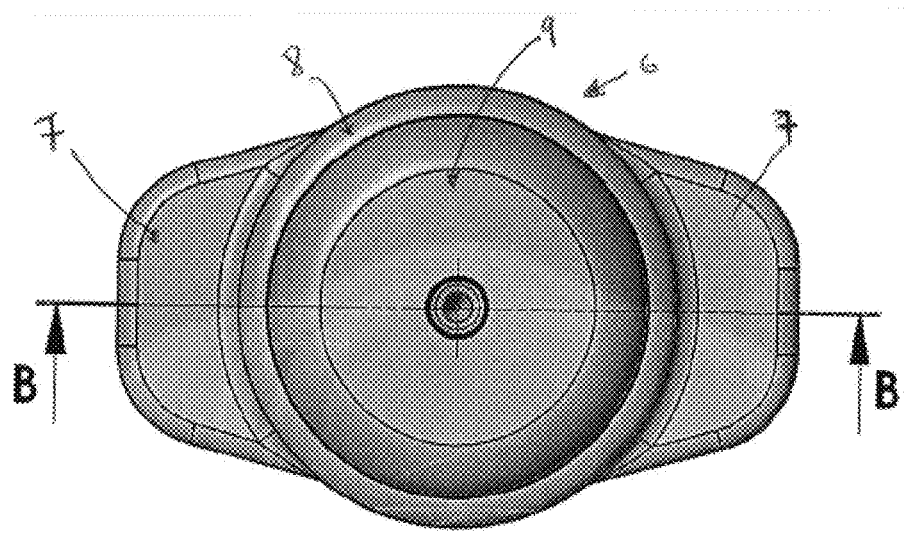
FIG. 2A is a top view of a valve according to the invention.

FIG. 2A is a top view illustrating the valve of the present invention. The air valve (6) having peripheral flanges (7), a valve seat (8) and a cap (9).

Figure 2B:
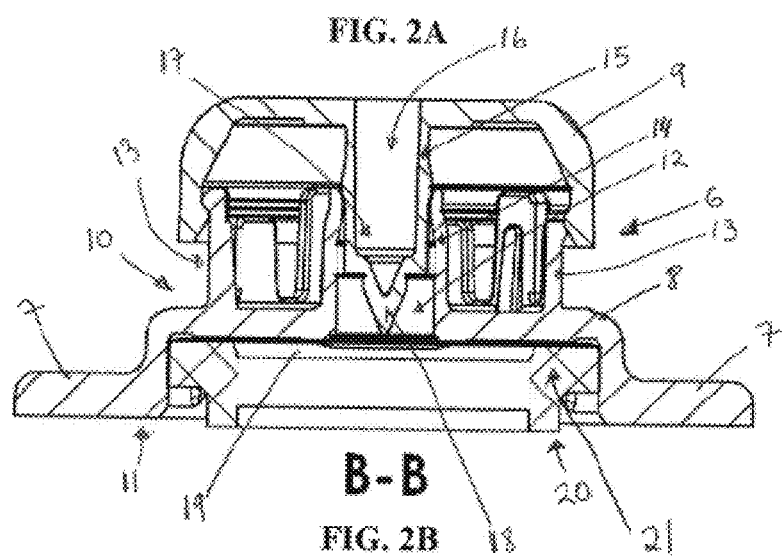
FIG. 2B is a cross sectional view of a valve according to the invention.

FIG. 2B is a cross sectional view illustrating a valve of the present invention in the stored position. The air valve (6) having peripheral flanges (7), a valve seat (8) and a cap (9). The valve body having a top end (10) and a bottom end (11), wherein the valve body has a through bore (12) extending from the top end (10) to the bottom end (11) of the valve body. The valve seat (8) includes a resilient engaging means (13), the valve seat further comprises a cylindrical collar (14) projecting upwards from said valve seat along the periphery of the through bore opening and forming an extension of the through bore. A substantially rigid valve stem (15) having a top end (16) and a bottom end (17). The valve stem (15) further comprising a penetrating tip (18) at bottom end of the stem for puncturing the container seal (19) fused on the annular portion (21) of proximal end of the container (20).

Figure 3A:
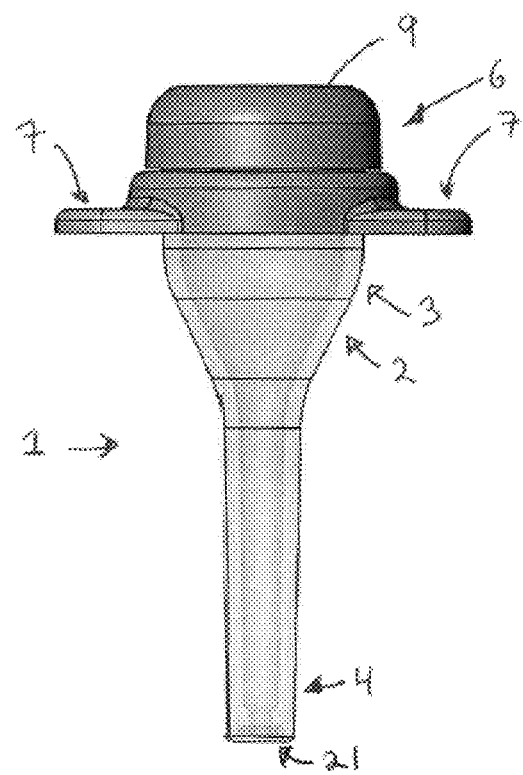
FIG. 3A is a side view of advice in the dispensing position according to the invention.

FIG. 3A is a side view illustrating the device of the present invention in the dispensing position according to the invention. A device (1) for storing and dispensing a topical pharmaceutical liquid having a substantially rigid elongated container (2), configured to hold the liquid therein, having a proximal end (3) and a distal end (4) with respective openings and the distal end of the container tapering into an applicator tip (21), the proximal end having an air valve (6), having flanges (7) and cap (9).

Figure 3B:
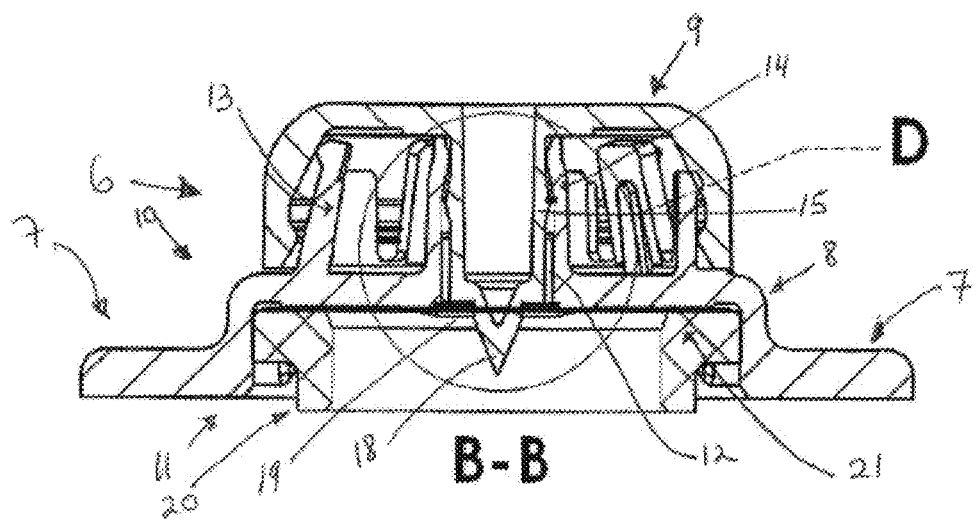
FIG. 3B is a cross sectional view of a valve in the dispensing position according to the invention.

FIG. 3B is a cross sectional view illustrating the valve of the present invention in the dispensing position according to the invention. The air valve (6) having peripheral flanges (7), a valve seat (8) and a cap (9). The valve body having a top end (10) and a bottom end (11), wherein the valve body has a through bore (12) extending from the top end (10) to the bottom end (11) of the valve body. The valve seat (8) includes a resilient engaging means (13), the valve seat further comprises a cylindrical collar (14) projecting upwards from said valve seat along the periphery of the through bore opening and forming an extension of the through bore. A substantially rigid valve stem (15) having a top end (16) and a bottom end (17). The valve stem (15) further comprising a penetrating tip (18) at bottom end of the stem which has punctured the container seal (19) fused on the annular portion (21) of proximal end of the container (20).

Figure 3C:
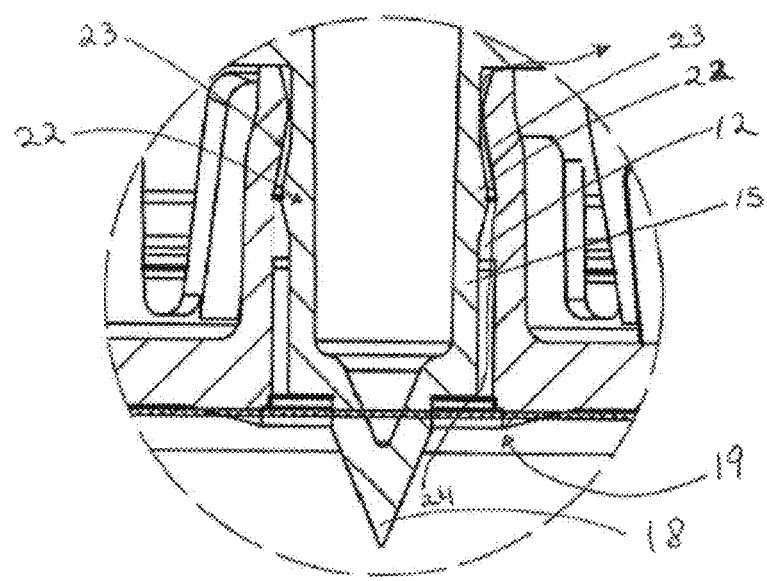
FIG. 3C is an enlarged cross sectional view of portion of a valve in the dispensing position, highlighted with broken circle D in FIG. 3B according to the invention.

FIG. 3C is an enlarged cross sectional view illustrating a portion of the valve in the dispensing position, highlighted with broken circle D in FIG. 3B according to the invention. The valve stem (15) has a means to form an airtight seal (22) against the inner wall (23) of the through bore (12). The valve stem (15) further comprising a penetrating tip (18) at bottom end of the stem which has punctured the container seal (19) to establish air communication where air can flow in the direction (24) through the valve between the interior of the container and the external environment.

Figure 4A:
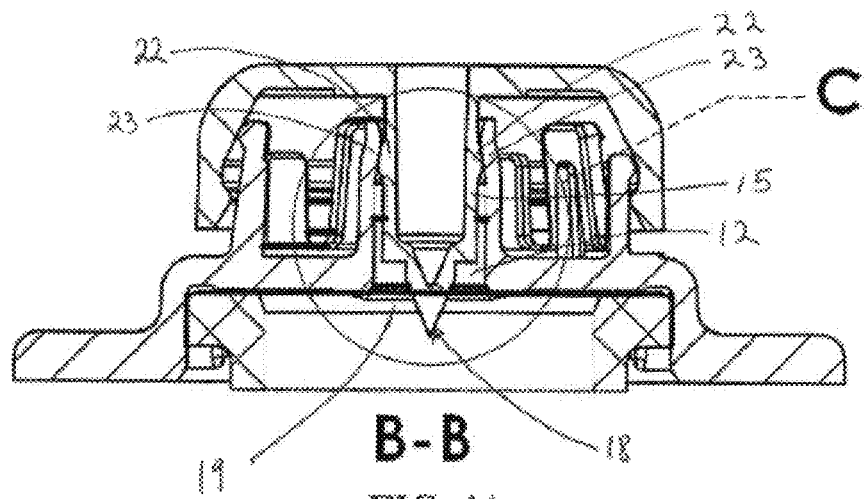
FIG. 4A is a cross sectional view of a valve in the sealed position according to the invention.

FIG. 4A is a cross sectional view illustrating the valve in the sealed position according to the invention. The valve stem (15) has a penetrating tip (18) at bottom end of the stem which has punctured the container seal (19). The valve stem (15) has a seal (22) which forms an air-tight seal against the inner wall (23) of the through bore (12) to prohibit air communication through the valve between the interior of the container and the external environment.

Figure 4B:
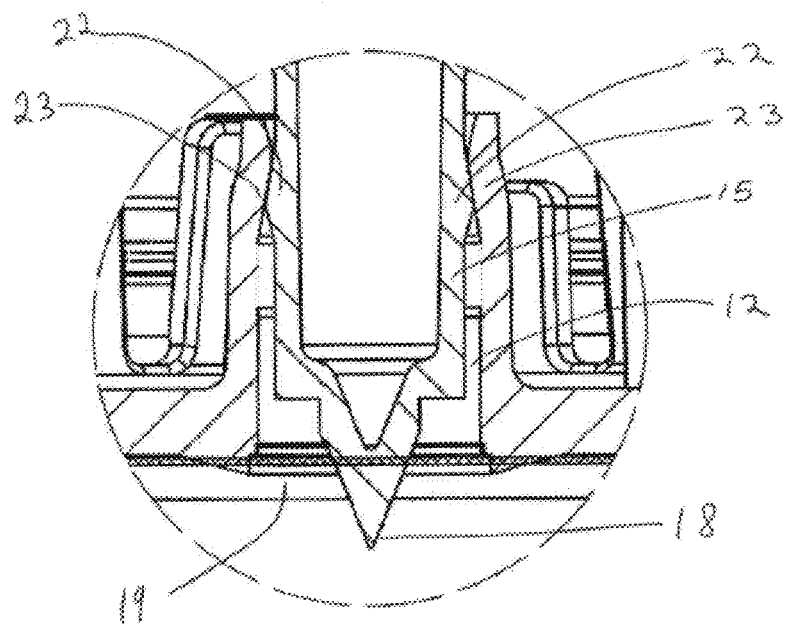
FIG. 4B is an enlarged cross sectional view of portion of a valve in the sealed position, highlighted with broken circle C in FIG. 4A according to the invention.

FIG. 4B is an enlarged cross sectional view illustrating a portion of the valve in the sealed position, highlighted with broken circle C in FIG. 4A according to the invention. The valve stem (15) has a penetrating tip (18) at bottom end of the stem which has punctured the container seal (19). The valve stem (15) has a seal (22) which forms an air-tight seal against the inner wall (23) of the through bore (12) to prohibit air communication through the valve between the interior of the container and the external environment.

Figure 5A:
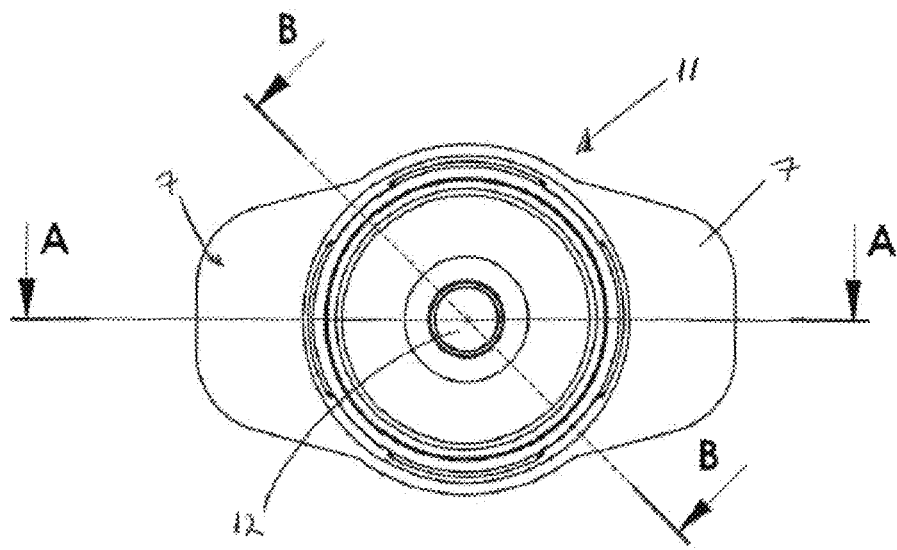
FIG. 5A is a bottom view of a valve seat according to the invention.

FIG. 5A is a bottom view illustrating the valve seat according to the invention. The bottom end of the valve body (11) has peripheral flanges (7) and a through bore (12) extending from the top end to the bottom end of the valve body.

Figure 5B:
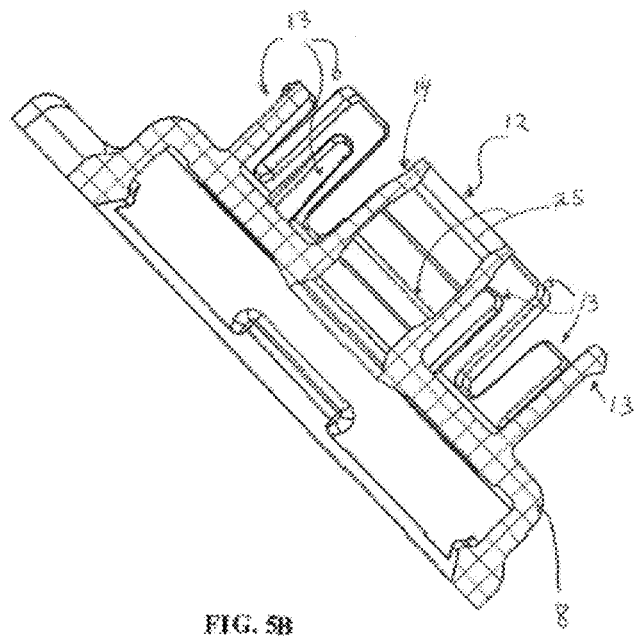
FIG. 5B is a cross sectional side view of a valve seat viewed through the plane B-B of FIG. 5A according to the invention.

FIG. 5B is a cross sectional side view illustrating the valve seat viewed through the plane B-B of FIG. 5A. The valve seat (8) includes a resilient engaging means (13) having different heights, the valve seat further comprises a cylindrical collar (14) projecting upwards from said valve seat along the periphery of the through bore opening and forming an extension of the through bore (12). The through bore has annular seals (25) on its inner wall.

Figure 5C:
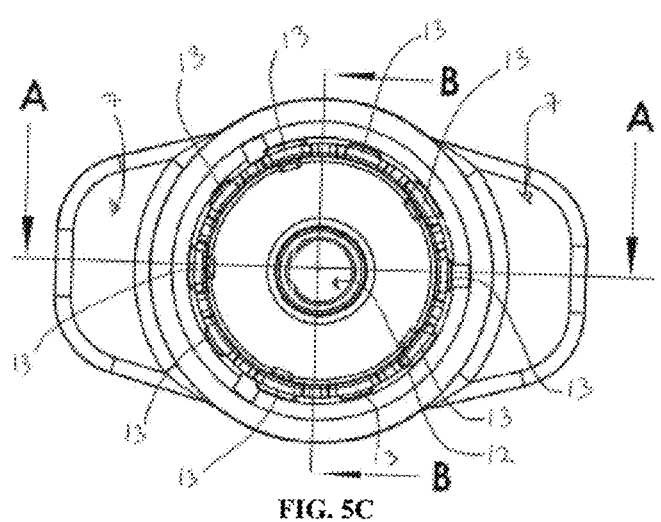
FIG. 5C is a top view of a valve seat according to the invention.
Figure 5D:
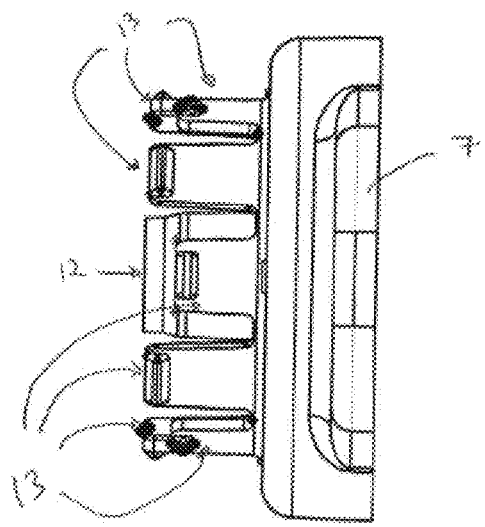
FIGS. 5D, 5E and 5F are different side views of a valve seat according to the invention.
Figure 5E:
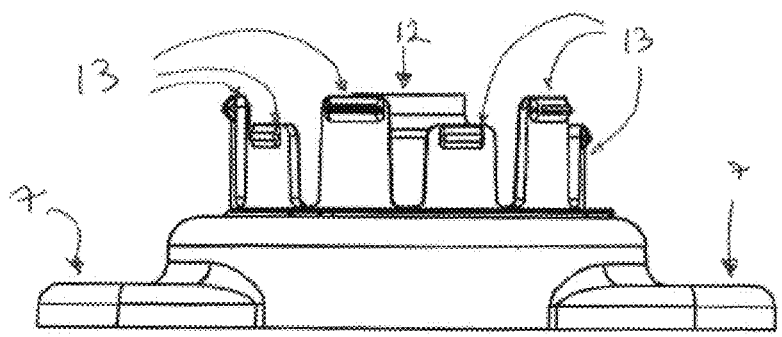
Figure 5F:
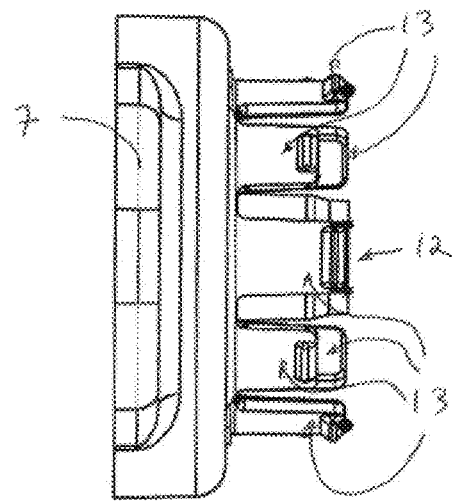

FIG. 5C is a top view illustrating the valve seat according to the invention and FIGS. 5D, 5E and 5F are different side views illustrating the valve seat of the invention. The valve seat includes a resilient engaging means (13) having different heights and peripheral flanges (7). The valve seat has a through bore (12).

Figure 5G:
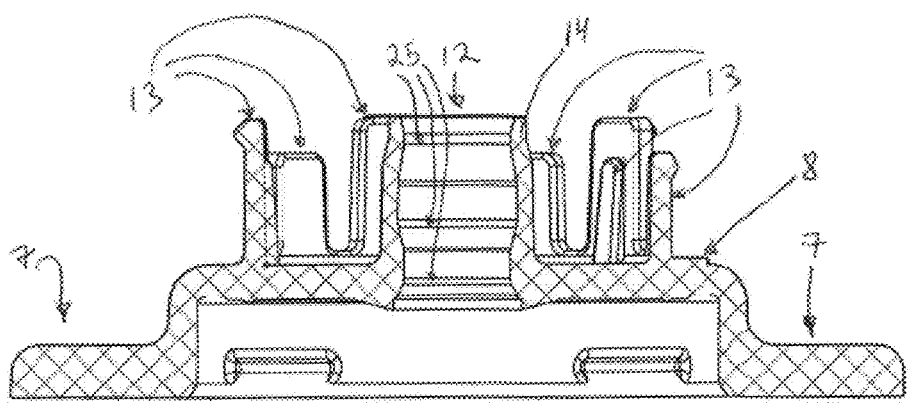
FIG. 5G is a cross sectional side view of a valve seat viewed through the plane A-A of FIG. 5A according to the invention.

FIG. 5G is a cross sectional side view illustrating the valve seat viewed through the plane A-A of FIG. 5A. The valve seat (8) includes a resilient engaging means (13) having different heights, the valve seat further comprises a cylindrical collar (14) projecting upwards from said valve seat along the periphery of the through bore opening and forming an extension of the through bore (12). The through bore has seals (25) on its inner wall.

Figure 6A:
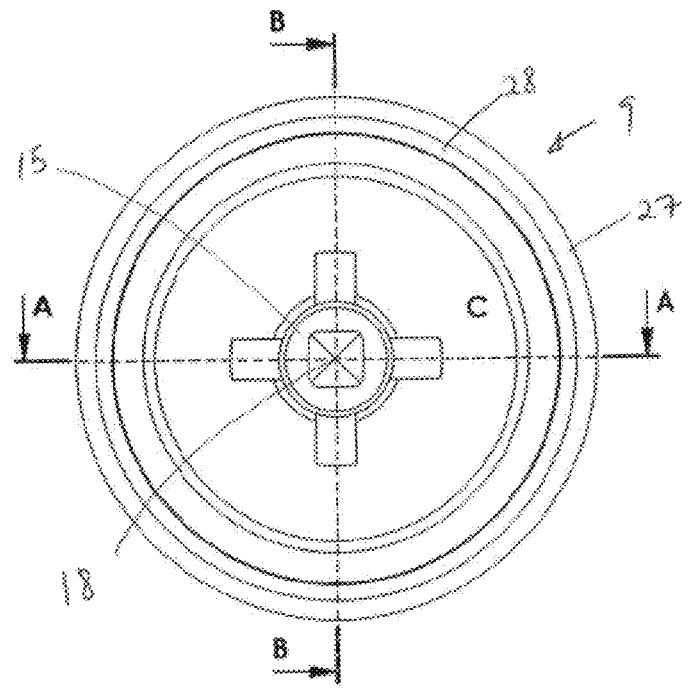
FIG. 6A is bottom view of a cap according to the invention.

FIG. 6A is bottom view illustrating the cap according to the invention. The cap (9) has a side wall (27), wherein the side wall has resilient engaging means (28) for engaging the corresponding engaging means on the valve seat. The valve stem (15) has a penetrating tip (18) at bottom end of the stem.

Figure 6B:
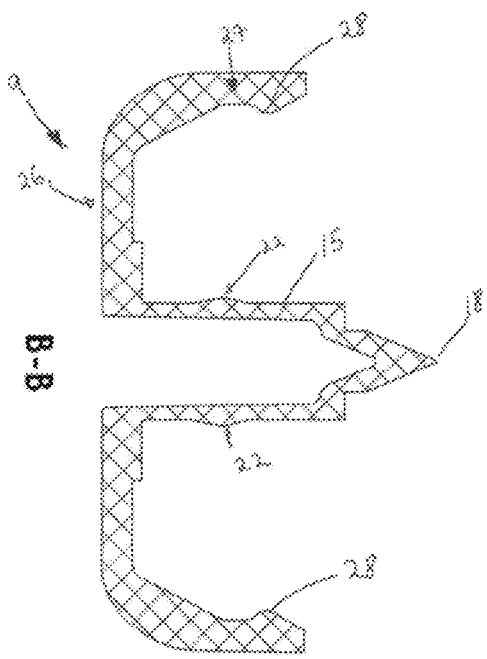
FIG. 6B is cross sectional view of a cap as viewed through the plane B-B of FIG. 6A according to the invention.
Figure 6C:
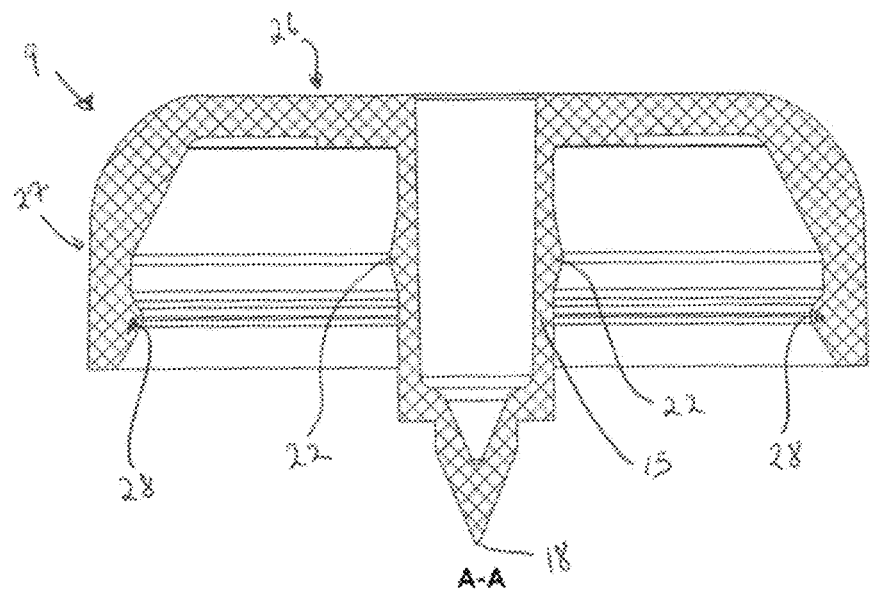
FIG. 6C is cross sectional view of a cap as viewed through the plane A-A of FIG. 6A according to the invention.

FIG. 6B is cross sectional view illustrating the cap as viewed through the plane B-B of FIG. 6A and FIG. 6C is cross sectional view illustrating the cap as viewed through the plane A-A of FIG. 6A. The cap (9) has a top (26) and a side wall (27), wherein the side wall has resilient engaging means (28) for engaging the corresponding engaging means on the valve seat. The valve stem (15) has a penetrating tip (18) at bottom end of the stem. The valve stem (15) has a means to form an airtight seal (22) and a penetrating tip (18) at bottom end of the stem which can punctured the container seal.

Figure 7A:
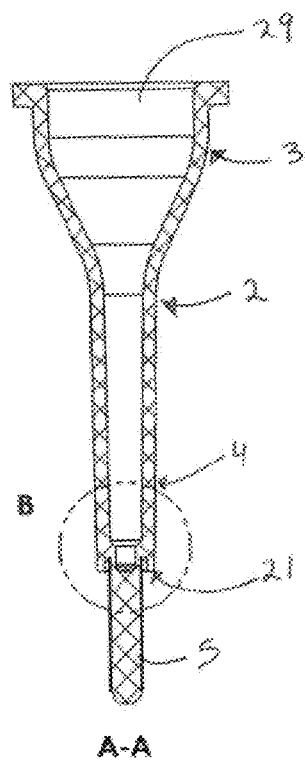
FIG. 7A is across sectional view of a portion of a container according to the invention.

FIG. 7A is cross sectional view of a portion of the container according to the invention. The elongated container (2), configured to hold the liquid therein, having a proximal end (3) and distal end (4) of the container tapering into an applicator tip (21). The proximal end of the container having an opening (29) and the distal opening of the container being closed by a closure means (5).

Figure 7B:
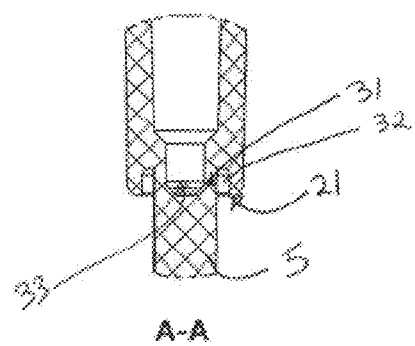
FIG. 7B is an enlarged view of a portion of FIG. 7A highlighted with broken circle B according to the invention.

FIG. 7B is an enlarged view of a portion of FIG. 7A highlighted with broken circle B according to the invention. The applicator tip (21) has a closure means (5) integrally moulded with the distal end of the applicator tip at a breakaway junction (31) situated in the recessed groove (32), so as to form an integral piece therewith, resulting in the break-away junction being recessed away from distal opening (33) of the container.

Figure 8:
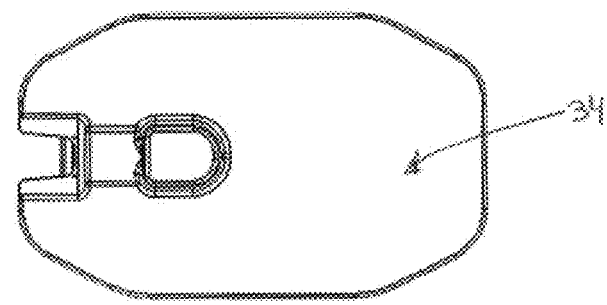
FIG. 8 is a side view of a lug according to the invention.

FIG. 8 is a side view of a lug according to the invention. The lug (34) can be attached to the break-away tip (not shown) to assist in manually removing the break-away tip.

Figure 9:
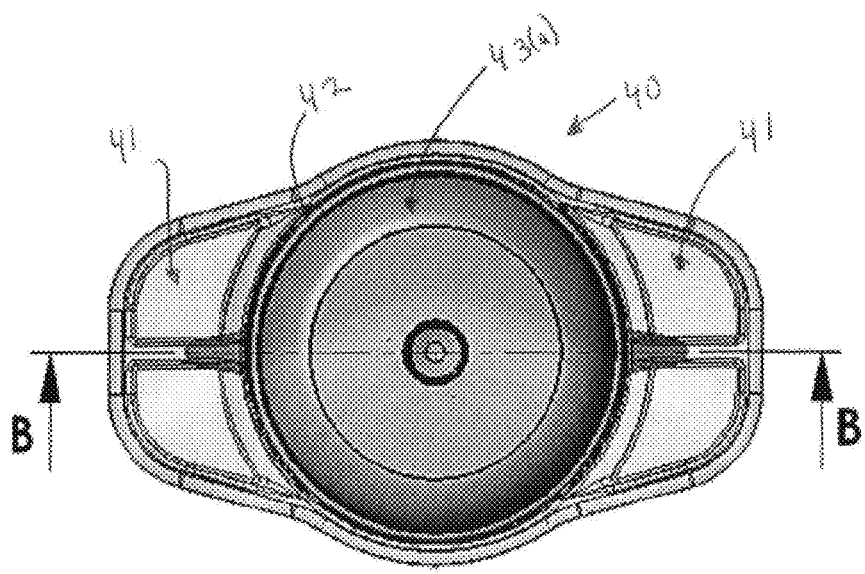
FIG. 9 is a top view of a valve according to another embodiment of the invention.

FIG. 9 is a top view illustrating a valve of the present invention. The air valve (40) having peripheral flanges (41), a valve seat (42) and a cap (43a).

Figure 10:
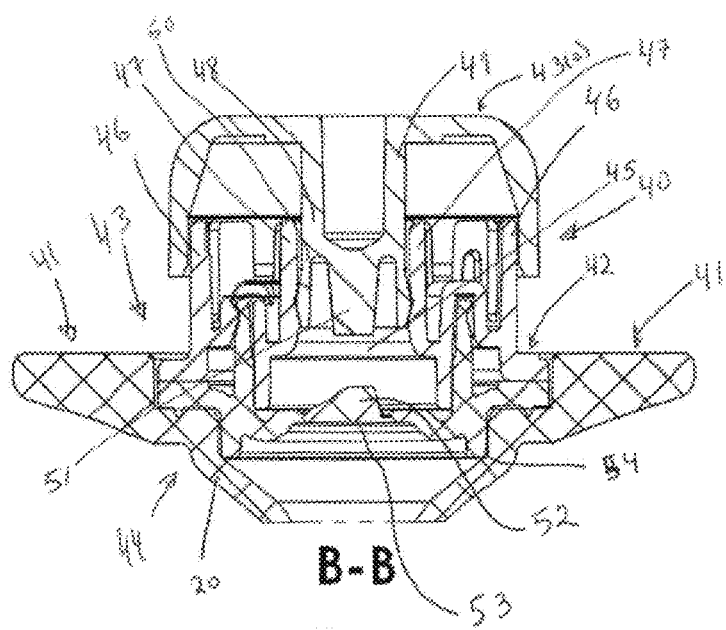
FIG. 10 is a cross sectional view of a valve in the stored position as viewed through the plane B-B of FIG. 9 according to another embodiment of the invention.

FIG. 10 is a cross sectional view illustrating the valve as viewed through the plane B-B of FIG. 9 in the stored position. The air valve (40) having peripheral flanges (41), a valve seat (42) and a cap (43a). The valve body having a top end (43) and a bottom end (44), wherein the valve body has a through bore (45) extending from the top end (43) to the bottom end (44) of the valve body. The valve seat (42) includes a resilient engaging means (46), the valve seat further comprises a cylindrical collar (47) projecting upwards from said valve seat along the periphery of the through bore opening and forming an extension of the through bore. A substantially rigid valve stem (48) having a top end (49) and a bottom end (50). The valve stem (48) further comprising a penetrating tip (51) at bottom end of the stem for pushing down on a protrusion (52) sticking out of the plane of the container seal (53) towards the penetrating tip so that pushing down of the penetrating tip on the protrusion, during dispensing, punctures the container seal (53) fused on the annular portion (54) of the proximal end of the container (20).

Figure 11:
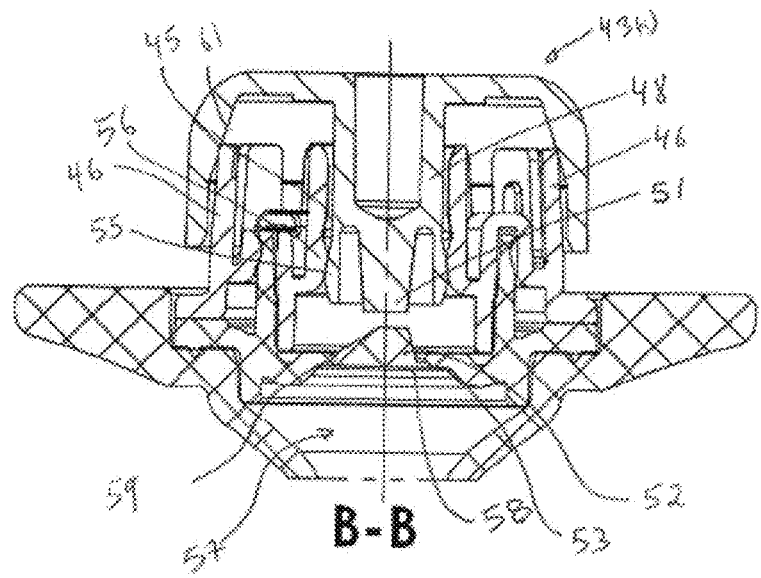
FIG. 11 is a cross sectional view of a valve in the sealed position as viewed through the plane B-B of FIG. 9 according to another embodiment of the invention.

FIG. 11 is a cross sectional view illustrating the valve as viewed through the plane B-B of FIG. 9 in the sealed position. The valve stem (48) has a penetrating tip (51) at bottom end of the stem which has punctured the container seal (53) (puncture not visible in this view). The top end of the valve stem (48) has a cap (43a). The resilient engaging means (46) engages the inside wall (61) of the cap (43a). A protrusion (52) sticking out of the plane of the container seal (53) towards the penetrating tip, the protrusion (52) is joined to the container seal (53) by means of a hinge (59) and a breakaway junction (58) which has been broken. The valve stem (48) has a seal (55) which forms an air-tight seal against the inner wall (56) of the through bore (45) to prohibit air communication through the valve between the interior of the container (57) and the external environment outside the container.

Figure 12:
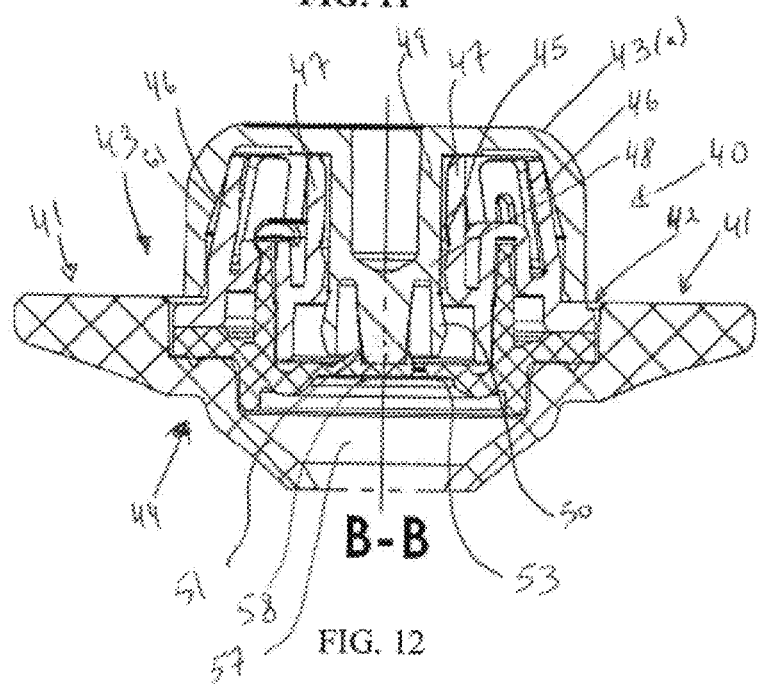
FIG. 12 is a cross sectional view of a valve in the dispensed position as viewed through the plane B-B of FIG. 9 according to another embodiment of the invention.

FIG. 12 is a cross sectional view illustrating the valve as viewed through the plane B-B of FIG. 9 in the dispensing position. The air valve (40) having peripheral flanges (41), a valve seat (42) and a cap (43(a)). The valve body having a top end (43) and a bottom end (44), wherein the valve body has a through bore (45) extending from the top end (43) to the bottom end (44) of the valve body. The valve seat (42) includes a resilient engaging means (46) which engages the inside wall (61) of the cap (43a). The valve seat further comprises a cylindrical collar (47) projecting upwards from said valve seat along the periphery of the through bore opening and forming an extension of the through bore. A substantially rigid valve stem (48) having a top end (49) and a bottom end (50). The valve stem (48) further comprising a penetrating tip (51) at bottom end of the stem. The breakaway junction (58) which has been broken on the container seal (53) and the protrusion (not shown) is situated in the interior of the container (57).

Figure 13:
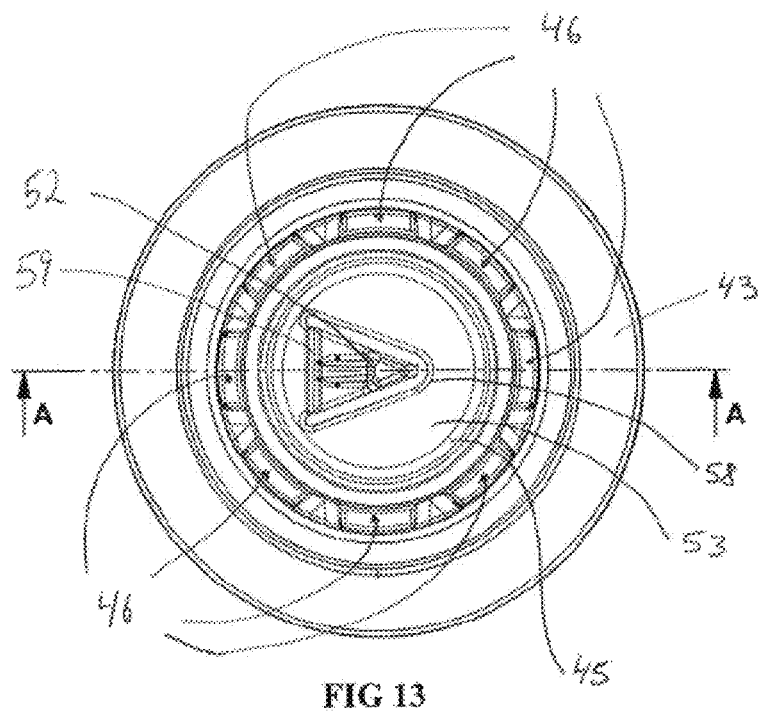
FIG. 13 is a top view illustrating of a valve seat according to another embodiment of the invention.

FIG. 13 is a top view illustrating a valve seat according to the invention. The valve seat (42) includes resilient engaging means (46) having different heights. The valve seat has a through bore (45) extending from the top end (43) to the bottom end (not shown) of the valve seat. The end of the through bore (45) at the bottom end of the valve seat, is sealed with a container seal (53). The annular portion of the valve seat (42) will be sealed to the proximal end of the container (not shown), when assembled. In the centre of the container seal (53) is a protrusion (52) sticking out of the plane of the container seal (53). The protrusion (52) is joined to the container seal (53) by means of a breakaway junction (58) which has a hinge (59) on one point of attachment to the container seal (53).

Figure 14:
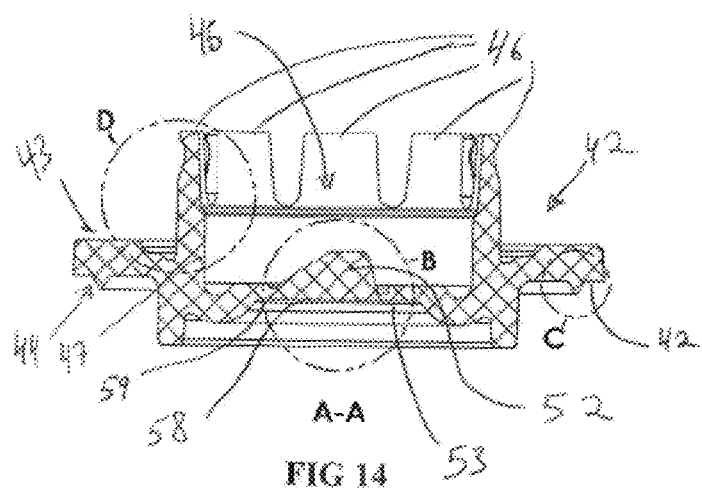
FIG. 14 is a cross sectional view of a valve seat as viewed through the plane A-A of FIG. 13 according to another embodiment of the invention.

FIG. 14 is a cross sectional side view illustrating a valve seat viewed through the plane A-A of FIG. 13 according to the invention. The valve seat (42) includes resilient engaging means (46). The valve seat has a through bore (45) extending from the top end (43) to the bottom end (44) of the valve seat. The end of the through bore (45) at the bottom end of the valve seat, is sealed with a container seal (53). The annular portion of the valve seat (42) will be sealed to the proximal end of the container (not shown), when assembled. In the centre of the container seal (53) is a protrusion (52) sticking out of the plane of the container seal (53). The protrusion (52) is joined to the container seal (53) by means of a breakaway junction (58) which has a hinge (59) on one point of attachment to the container seal (53). The valve seat (42) further comprises a cylindrical collar (47) projecting upwards from said valve seat along the periphery of the through bore opening and forming an extension of the through bore.

Figure 15:
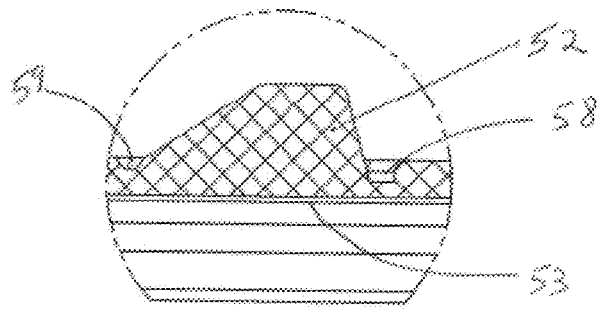
FIG. 15 is an enlarged view of a portion of FIG. 14 highlighted with broken circle B according to the invention.

FIG. 15 is an enlarged view of a portion of FIG. 14 highlighted with broken circle B according to the invention. The protrusion (52) is joined to the container seal (53) by means of a breakaway junction (58) which has a hinge (59) on one point of attachment to the container seal (53).

Figure 16:
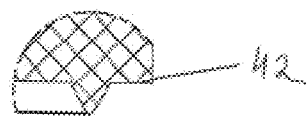
FIG. 16 is an enlarged view of a portion of FIG. 14 highlighted with broken circle C according to the invention.

FIG. 16 is an enlarged view of a portion of FIG. 14 highlighted with broken circle C according to the invention. The annular portion of the valve seat (42) will be sealed to the proximal end of the container (not shown), when assembled.

Figure 17:
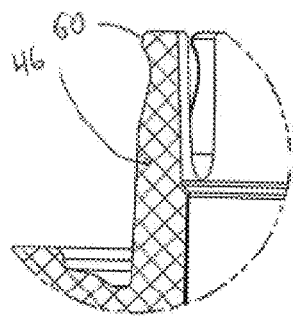
FIG. 17 is an enlarged view of a portion of FIG. 14 highlighted with broken circle D according to the invention.

FIG. 17 is an enlarged view of a portion of FIG. 14 highlighted with broken circle D according to the invention.

The resilient engaging means (46) has an outward protrusion (60) meant to engage a resilient engaging means on the cap (not shown).

Figure 18:
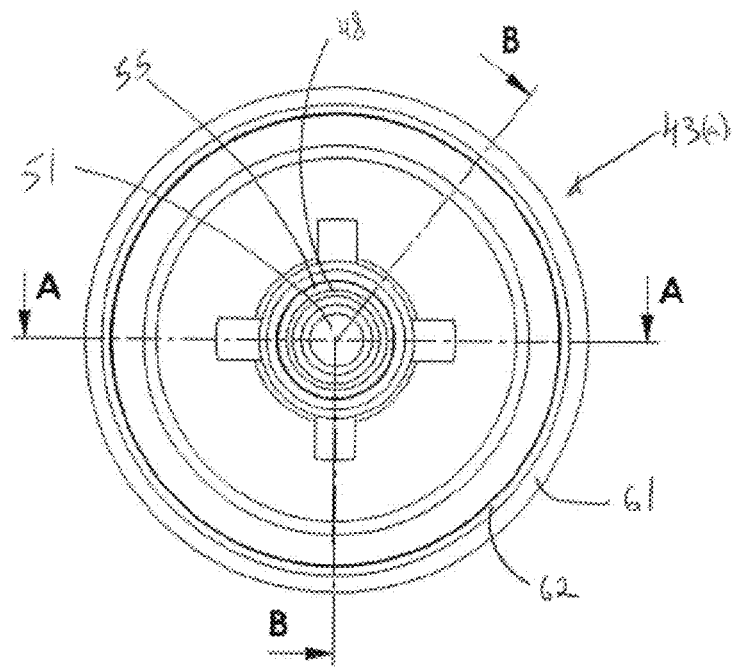
FIG. 18 is a bottom view illustrating a cap according to another embodiment of the invention.

FIG. 18 is a bottom view illustrating a cap according to the invention. The cap (43a) has a side wall (61), wherein the side wall has resilient engaging means (62) for engaging the corresponding engaging means on the valve seat (not shown). The valve stem (48) has a penetrating tip (51) at bottom end of the stem and it has a radial seal (55) which forms an air-tight seal against the inner wall of the through bore when in the sealed position (not shown)

Figure 19:
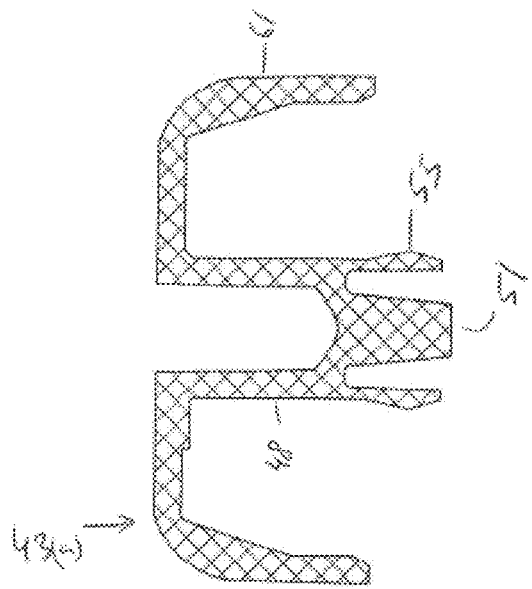
FIG. 19 is a cross sectional view of a valve seat as viewed through the plane B-B of FIG. 18 according to another embodiment of the invention.

FIG. 19 is a cross sectional side view illustrating a valve seat viewed through the plane B-B of FIG. 18 according to the invention. The cap (43a) has a side wall (61), wherein the side wall has resilient engaging means (55) which forms an air-tight seal against the inner wall (not shown) of the through bore (not shown), when in the sealing position. The valve stem (48) has a penetrating tip (51) at bottom end of the stem and it has a radial seal (not shown) which forms an air-tight seal against the inner wall of the through bore when in the sealed position (not shown).

Figure 20:
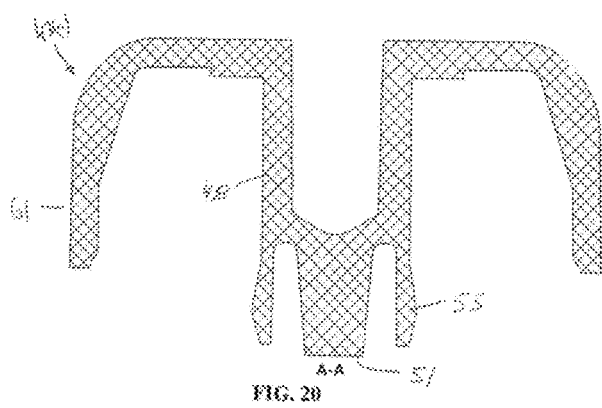
FIG. 20 a cross sectional view of a valve seat as viewed through the plane A-A of FIG. 18 according to another embodiment of the invention.

FIG. 20 is a cross sectional side view illustrating a valve seat viewed through the plane A-A of FIG. 18 according to the invention. The cap (43a) has a side wall (61), wherein the side wall has resilient engaging means (55) which forms an air-tight seal against the inner wall (not shown) of the through bore (not shown), when in the sealing position. The valve stem (48) has a penetrating tip (51) at bottom end of the stem and it has a radial seal (not shown) which forms an air-tight seal against the inner wall of the through bore when in the sealed position (not shown).

Figure 21:
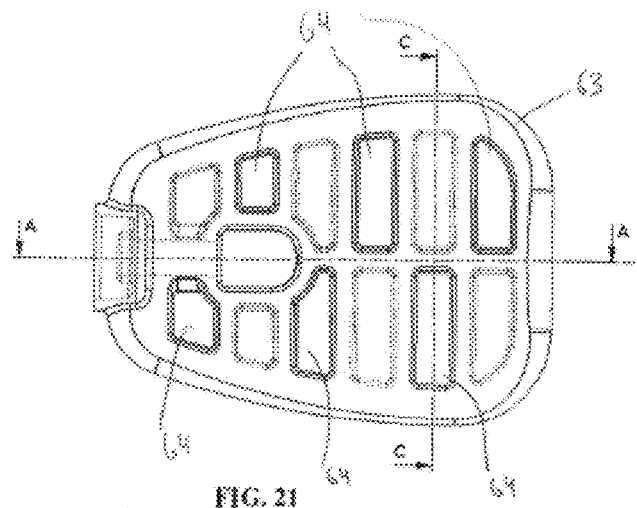
FIG. 21 is a front view of a lug according to another embodiment of the invention.

FIG. 21 is a front view of a lug according to the invention. The lug (63) can be attached to the break-away tip (not shown) to assist in manually removing the break-away tip. The lug (63) has a series of indentations (64) to assist in gripping the tug by the users fingers.

Figure 22:
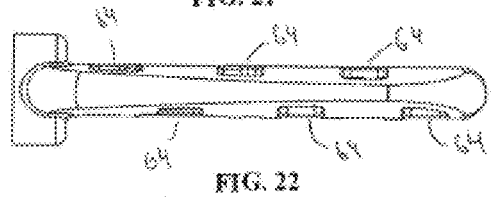
FIG. 22 is a side view of a lug according to another embodiment of the invention.

FIG. 22 is a side view of a lug according to the invention as illustrated in FIG. 21. The lug (63) has a series of indentations (64) to assist in gripping the tug by the users fingers.

Figure 23:
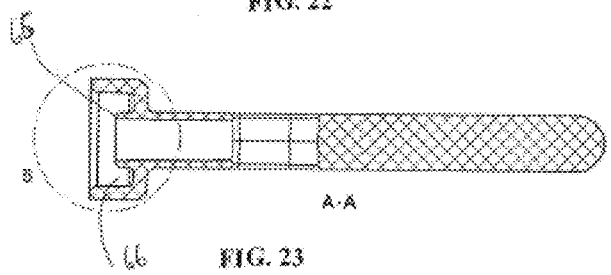
FIG. 23 is a cross sectional view of a lug as viewed through the plane A-A of FIG. 21 according to another embodiment of the invention.

FIG. 23 is a cross sectional side view illustrating a lug viewed through the plane A-A of FIG. 21 according to the invention. The lug has a breakaway junction (65) situated in the recessed groove (66).

Figure 24:
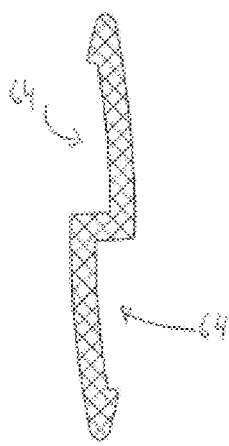
FIG. 24 is a cross sectional view of a lug as viewed through the plane C-C of FIG. 21 according to another embodiment of the invention.

FIG. 24 is a cross sectional side view illustrating a lug viewed through the plane C-C of FIG. 21 according to the invention. The has a series of indentations (64) to assist in gripping the tug by the users fingers.

Figure 25:
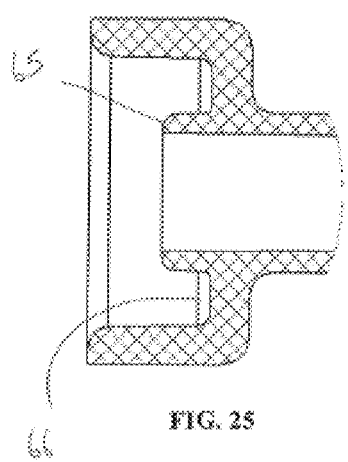
FIG. 25 is an enlarged view of a portion of FIG. 23 highlighted with broken circle B according to the invention.

FIG. 25 is an enlarged view of a portion of FIG. 23 highlighted with broken circle B according to the invention. The lug has a breakaway junction (65) situated in the recessed groove (66).

In an embodiment of the invention is a device having an elongated container defining an interior space and configured to hold the liquid therein, having a proximal end and a distal end with respective openings and a passage extending between the openings, the proximal opening being closed by a container seal and the distal end of the container tapering into an applicator tip which is integral therewith. The device has an air valve sealingly coupled to the proximal end of the container, wherein the air valve comprises a penetrating tip which can puncture the container seal, the valve being illustrated in a stored position in which the seal is not punctured by the penetrating tip. The air valve having a spring which biases the penetrating tip away from the container seal. The air valve also has a cap having a top and side wall whose interior is of generally cylindrical configuration and of diameter slightly greater than the outside diameter of the proximal end of the container, the cap being sealingly coupled to the proximal end of the container and has an air inlet which opens and permits air communication to be formed when the top of cap is pressed towards the container. The distal opening of the container being closed at by a closure mean shaving lugs.

In an embodiment of the invention is a device having an elongated container defining an interior space and configured to hold the liquid therein, having a proximal end with an opening being closed by a container seal. The device has an air valve sealingly coupled to the proximal end of the container, wherein the air valve comprises a penetrating tip which can puncture the container seal, the valve being illustrated in a stored position in which the seal is not punctured by the penetrating tip. The air valve having a spring which biases the penetrating tip away from the container seal. The air valve also has a cap having a top and side wall whose interior is of generally cylindrical configuration and of diameter slightly greater than the outside diameter of the proximal end of the container, the cap has an air inlet which opens and permits air communication to be formed when the top of cap is pressed towards the container.

In an embodiment of the invention is a device having an elongated container defining an interior space and configured to hold the liquid therein, having a proximal end with an opening being closed by a container seal. The device has an air valve sealingly coupled to the proximal end of the container, wherein the air valve comprises a penetrating tip which can puncture the container seal, the valve being illustrated in a stored position in which the seal is not punctured by the penetrating tip. The air valve having a spring which biases the penetrating tip away from the container seal. The air valve also has a cap having a top and side wall whose interior is of generally cylindrical configuration and of diameter slightly greater than the outside diameter of the proximal end of the container, the cap has an air inlet which opens and permits air communication to be formed when the top of cap is pressed towards the container.

In an embodiment of the invention is a device having an elongated container defining an interior space and configured to hold the liquid therein, having a proximal end with an opening being closed by a container seal and a distal end having an opening closed by a closure means having lugs. The device has an air valve coupled to the proximal end of the container. The air valve having a cap having a top and side wall slidingly coupled to the proximal end of the container. The valve being in a stored position in which the seal is not punctured by the penetrating tip. Inside the interior space between the cap and container seal is a spring sealing coupled to the proximal end of the container and made of resilient material which biases the penetrating tip away from the container seal, the spring having a penetrating tip in its interior. The spring whose interior is of generally cylindrical configuration and of diameter slightly greater than the outside diameter of the proximal end of the container and has an air inlet which opens and permits air communication to be formed when the top of cap is pressed towards the container. The spring has a penetrating tip (90) in its interior, protruding from its top which can puncture the container seal when the cap is pressed down in the direction towards the container seal.

In an embodiment of the invention is a device having an elongated container defining an interior space and configured to hold the liquid therein, having a proximal end with an opening being closed by a container seal. The device has an air valve coupled to the proximal end of the container. The air valve having a cap having a top and side wall slidingly coupled to the proximal end of the container. The cap has a penetrating tip in its interior, protruding from its top which can puncture the container seal when the cap is pressed down in the direction towards the container seal. The valve being in a stored position in which the seal is not punctured by the penetrating tip. Inside the interior space between the cap and container seal is a spring sealing coupled to the proximal end of the container and coupled to the interior of the cap. The spring being made of resilient material which biases the cap and penetrating tip away from the container seal. The spring whose interior is of generally cylindrical configuration and of diameter slightly greater than the outside diameter of the proximal end of the container and has an air inlet which opens and permits air communication to be formed when the top of cap is pressed towards the container.

In an embodiment of the invention is a device for storing and dispensing a pharmaceutical liquid comprising: A) a substantially rigid elongated container defining an interior space and configured to hold the liquid therein, having a proximal end and a distal end with respective openings and a passage extending between the openings, the proximal opening being closed by a container seal and the distal end of the container tapering into an applicator tip which is integral therewith; and B) an air valve sealingly coupled to the proximal end of the container, wherein the air valve comprises a penetrating tip which can puncture the container seal to enabling air communication to be formed through the valve between the interior of the container and the external environment, the valve being positionable in a stored position in which the seal is not punctured by the penetrating tip, and in a dispensed position in which the seal is punctured by the penetrating tip and the air communication is formed, and in a sealed position in which the seal is punctured by the penetrating tip and an airtight seal is formed to prohibit air communication being formed; and wherein dispensing the liquid through the applicator tip is controlled by the air communication.

In an embodiment of the invention, there is provided a device wherein the valve further comprises a spring which biases the penetrating tip away from the container seal.

In an embodiment of the invention, the engaging means of the valve seat also act as the spring which biases the penetrating tip away from the container seal.

In an embodiment of the invention, there is provided a device wherein the air valve further comprises a cap having a top and side wall whose interior is of generally cylindrical configuration and of diameter slightly greater than the outside diameter of the proximal end of the container, said cap being sealingly coupled to the proximal end of the container and further comprises an air inlet which opens and permits air communication to be formed when the top of cap is pressed towards the container and which closes prohibiting air communication when the top of the cap moves away from the container.

In an embodiment of the invention, there is provided a device wherein the air inlet is configured to open by elastically deforming to create a tear in the cap forming air communication when the cap is pressed and to close by self-reclosing to return opposite edges of said tear to a substantially contiguous closed condition prohibiting air communication when the cap is not pressed.

In an embodiment of the invention, there is provided a device wherein the cap is made of resilient material.

In an embodiment of the invention, there is provided a device wherein the penetrating tip is located in the interior of the cap extending generally axially from its top so that when the cap is pressed towards the container, the penetrating tip punctures the container seal.

In an embodiment of the invention, there is provided a device wherein the penetrating tip is coupled to the proximal end of the container situated in the interior of the cap so that when the cap is pressed towards the container, the penetrating tip moves towards the container causing it to puncture the container seal.

In an embodiment of the invention, there is provided a device wherein the air valve further comprises a valve body having a top end and a bottom end, wherein the bottom end of the valve body and the proximal end of the container are sealingly coupled by an air tight connector, and the top end of the valve body has a valve seat, the valve body having a through bore extending from the top end to the bottom end of the valve body, wherein the through bore has an inner wall defining a passage through the valve body.

In an embodiment of the invention, there is provided a device wherein the air valve further comprises a substantially rigid valve stem, wherein the penetrating tip is attached at one end of the valve stem and a cap is attached at the opposite end of the valve stem.

In an embodiment of the invention, there is provided a device wherein the valve stem is slidably receivable in the through bore and movable axially in the through bore towards and away from the outer surface of the container seal.

In an embodiment of the invention, there is provided a device wherein the penetrating tip is movable perpendicularly to the outer surface of the container seal In an embodiment of the invention, there is provided a device wherein the valve seat further comprises a cylindrical collar projecting upwards from said valve seat along the periphery of the through bore opening and forming an extension of the through bore.

In an embodiment of the invention, there is provided a device wherein the valve stem and through bore have means to form an airtight seal with each other.

In an embodiment of the invention, there is provided a device wherein the inner wall of the through bore has a means to form an airtight seal against the valve stem.

In an embodiment of the invention, there is provided a device wherein the valve stem has a means to form an airtight seal against the inner wall of the through bore.

In an embodiment of the invention, there is provided a device wherein the means to form an airtight seal between the valve stem and through bore comprises at least one annular ridge and at least one corresponding annular groove to sealably connect to the annular ridge.

In an embodiment of the invention, there is provided a device wherein the means to form an airtight seal between the valve stem and through bore comprises a circumferential edge on the valve stem having a seal which can bear against a corresponding seal on the inner wall of the through bore to create an air-tight seal.

In an embodiment of the invention, there is provided a device wherein the liquid is of low viscosity.

In an embodiment of the invention, there is provided a device wherein the interior of the container and the external environment are at about atmospheric pressure when the valve is in the storage and dispensed position.

In an embodiment of the invention, there is provided a device wherein the liquid is a topical veterinary liquid.

In an embodiment of the invention, there is provided a device wherein the liquid is for a pharmaceutically acceptable period of time.

In an embodiment of the invention, there is provided a device wherein the container is a pre-filled disposable container.

In an embodiment of the invention, there is provided a device wherein the proximal end of the container is connected to the bottom of the valve by means of a snap fit connection or mechanical connection.

In an embodiment of the invention, there is provided a device wherein the air tight connector is a sealing ring.

In an embodiment of the invention, there is provided a device wherein virtually all the liquid in the container is discharged through the applicator tip when the valve is in its dispensed position and the container is held in a near vertical orientation.

In an embodiment of the invention, there is provided a device wherein the outer edge of the container seal is fused or welded, to an adjacent annular portion of the container.

In an embodiment of the invention, there is provided a device wherein the container seal is configured to elastically distend to pass the penetrating tip through a tear in the container seal and to be self-reclosing by returning opposite edges of said tear to a substantially contiguous closed condition after withdrawal of the penetrating tip from the tear.

In an embodiment of the invention, there is provided a device wherein the applicator tip is selected from the group consisting of a dropper tip, a Uro-Jet tip, a needleless tip, a male Luer-Lock tip, a female Luer-Lock tip, an absorbent cotton tip, an absorbent band tip, an absorbent foam tip, a multi-hole distributor, or a brush tip.

In an embodiment of the invention, there is provided a device wherein the distal end of the container tapering into an applicator tip is an unobstructed opening of small size such that the liquid will not flow through by force of gravity when the applicator tip is directed downwardly and the container seal is not punctured by the penetrating tip or when the valve is in the sealed position.

In an embodiment of the invention, there is provided a device wherein the applicator tip is downwardly directed when in use.

In an embodiment of the invention, there is provided a device wherein the applicator tip's internal diameter controls the size of the droplet.

In an embodiment of the invention, there is provided a device wherein the dispensing of the liquid through the applicator tip is under gravity flow and under atmospheric air pressure.

In an embodiment of the invention, there is provided a device wherein the device manually regulates and stops the gravity flow of liquid from the applicator tip when valve is in the sealed position.

In an embodiment of the invention, there is provided a device wherein the penetrating tip is outside the container prior to creating the air communication, and wherein movement of the valve stem by force on the cap provides contact between the container seal and the penetrating tip sufficient to create the air communication.

In an embodiment of the invention, there is provided a device wherein the cap further has periphery rim engageable with the valve body.

In an embodiment of the invention, there is provided a device wherein the cap periphery is of resilient material.

In an embodiment of the invention, there is provided a device wherein the valve stem is coupled to a spring for biasing the penetrating tip away from the container seal.

In an embodiment of the invention, there is provided a device wherein the valve body has peripheral flanges to be used as grips for a user's index and middle finger.

In an embodiment of the invention, there is provided a device wherein the valve seat includes a resilient engaging means, said engaging means projecting upwards from said valve seat and being of two different heights.

In an embodiment of the invention, there is provided a device wherein the distal opening of the container being closed by a closure means.

In an embodiment of the invention, there is provided a device wherein the container seal and closure means are sealed when the valve is in the storage position so as to protect the liquid in the container against oxygen and/or humidity.

In an embodiment of the invention, there is provided a device wherein the penetrating tip is moved towards the container seal to establish air communication between the container and the through bore.

In an embodiment of the invention, there is provided a device wherein the valve is a manual operated valve.

In an embodiment of the invention, there is provided a device wherein the valve can be operated by pressing manually on the cap with the thumb while holding the valve seat between flanges that are conveniently provided thereon.

In an embodiment of the invention, there is provided a device wherein the valve is a one-way valve permitting inflow of air through the valve into the container and prohibiting outflow of liquid out of the container through the valve, when the valve is in the dispense position.

In an embodiment of the invention, there is provided a device wherein the inside of the container is under a partial vacuum which holds the solution inside the container against the force of gravity, when the valve is in the sealed position.

In an embodiment of the invention, there is provided a device wherein the applicator tip further comprises a closure means which is adapted for being manually opened.

In an embodiment of the invention, there is provided a device wherein the closure means is a break-away tip.

In an embodiment of the invention, there is provided a device wherein the valve stem having the penetrating tip is movable axially in the through bore towards the outer surface of the container seal In an embodiment of the invention, there is provided a device wherein the valve stem having the penetrating tip is movable axially in the through bore away from the outer surface of the container seal once the seal is punctured.

In an embodiment of the invention, there is provided a device wherein the valve stem is slidably receivable in a through bore integrally formed in the valve body In an embodiment of the invention, there is provided a device wherein the through bore defines an air passage through the valve body In an embodiment of the invention, there is provided a device wherein the through bore is in the form of a through tubular cylinder essentially perpendicular to the surface of the container seal.

In an embodiment of the invention, there is provided a device wherein the through bore is in the form of a through tubular cylinder having a central axis, and outer surface and an inner surface that defines an interior space which guides the valve stem In an embodiment of the invention, there is provided a device wherein the valve stem having the penetrating tip is movable perpendicularly to the outer surface of the container seal wherein the valve stem having the penetrating tip is movable axially in the through bore towards the outer surface of the container seal In an embodiment of the invention, there is provided a device wherein the valve stem having the penetrating tip is movable axially in the through bore away from the outer surface of the container seal once the seal is punctured.

In an embodiment of the invention, there is provided a device wherein the applicator tip has a proximal end near the distal end of the container and a distal end which is near the distal opening of the container having an annular recessed groove in the wall of the applicator, the break-away tip is integrally moulded with the distal end of the applicator tip at a breakaway junction situated in the recessed groove, so as to form an integral piece therewith, resulting in the break-away junction being recessed away from distal opening of the container.

In an embodiment of the invention, there is provided a device wherein the container is made from a polymer composition comprising a thermoplastic cyclic olefin polymer or copolymer and a thermoplastic elastomer.

In an embodiment of the invention, there is provided a device wherein the valve is made from a polymer composition comprising a thermoplastic cyclic olefin polymer or copolymer and a thermoplastic elastomer.

In an embodiment of the invention, there is provided a device wherein the container seal is made from a polymer composition comprising a thermoplastic cyclic olefin polymer or copolymer and a thermoplastic elastomer.

In an embodiment of the invention, there is provided a device wherein the container is made of a nor-bornene copolymer.

In an embodiment of the invention, there is provided a device wherein the valve is made of elastomeric materials. Examples of elastomeric materials that can be utilized include, but are not limited to, polyurethanes, polypropylene-EPDM, other polypropylenes, polysiloxane and/or silicone materials, butyl materials, isoprenes, neoprenes, polyethylenes and various copolymers, composites, blends or other combinations of such materials. Examples of plastics that can be utilized for valve stem and/or valve body include, but are not limited to, polyethylenes, polypropylenes, polycycloolefines, polyvinyl chlorides (PVC), polyamides (including aliphatic and aromatic variants), polyesters, polycarbonates, polyacrylates, polyurethanes, copolymers, blends, composites and combinations thereof.

In an embodiment of the invention, there is provided a device wherein the container seal is made of a barrier film is selected from the group consisting of a polyester film, a polyamide film, a polyvinylchloride film, a polychlorotrifluorethylene film. a halogenated polymer film, a non-halogenated polyisobutylene-isoprene rubber film, a polyvinylidene chloride film, a cyclic olefin copolymer film, a polypropylene film, a polyethylene film, a polytetrafluoroethylene film, a silicone oxide coated polymer film, an aluminum oxide coated polymer film, and combinations thereof.

In an embodiment of the invention, there is provided a device substantially as hereinbefore described with reference to and as illustrated in the accompanying figures.

In an embodiment of the invention, there is provided a device for storing and dispensing a topical pharmaceutical liquid comprising: A) a substantially rigid elongated container, configured to hold the liquid therein, having a proximal end and a distal end with respective openings and a passage extending between the openings, the proximal end of the container having an external radial surface, the proximal opening being closed by a container seal and the distal end of the container tapering into an applicator tip, the distal opening being closed by a closure means; and B) an air valve comprising (a) a valve body having a top end and a bottom end, wherein the bottom end of the valve body and the proximal end of the container are sealed together, wherein the valve body has peripheral flanges, wherein the top end of the valve body has a valve seat including an area defining a through bore extending from the top end to the bottom end of the valve body, wherein the through bore has an inner wall and has a seal protruding out from said inner wall, wherein the valve seat includes a resilient engaging means, said engaging means projecting upwards from said valve seat and being of two different heights; the valve seat further comprises a cylindrical collar projecting upwards from said valve seat along the periphery of the through bore opening and forming an extension of the through bore; and (b) a substantially rigid valve stem having a top end and a bottom end, wherein the stem is moveable within the through bore towards the top or bottom end of the through bore, the valve stem has a circumferential edge and has seal on said circumferential edge which can bear against a corresponding seal on the inner wall of the through bore; the valve stem further comprising a penetrating tip at bottom end of the stem for puncturing the container seal when the penetrating tip is moved towards the container seal to establish air communication through the valve between the interior of the container and the external environment; and a cap at the top end of the stem having a top and side wall, wherein the side wall has resilient engaging means for engaging the corresponding engaging means on the valve seat; wherein the valve has a spring for biasing the penetrating tip away from the container seal, wherein the valve has a configuration which is a stored position, an dispensed position or a sealed position; the stored position is when the valve is configured such that the container seal is not punctured by the penetrating tip; the dispensed position is when the valve is configured such that the penetrating tip punctured the container seal and the seals on the valve stem and the inner wall of the through bore do not create an air-tight seal, permitting air communication to be formed through the valve between the interior of the container and the external environment resulting in the liquid being dispensed from the container; and the sealed position is when the valve is configured such that the penetrating tip has moved away from the container and the seal on the valve stem bears against the corresponding seal on the inner wall of the through bore to create an air-tight seal prohibiting air communication to be formed through the valve between the interior of the container and the external environment resulting in no liquid being dispensed from the container; wherein the engaging means of the a cap and the valve seat are engaged with each other to hold the penetrating tip in position when the valve is in the stored or sealed position; and wherein the applicator tip has a proximal end near the distal end of the container and a distal end which is near the distal opening of the container having an annular recessed groove in the wall of the applicator; and wherein the closure means is a break-away tip integrally moulded with the distal end of the applicator tip at a breakaway junction situated in the recessed groove, so as to form an integral piece therewith, resulting in the break-away junction being recessed away from distal opening of the container.

In an embodiment of the invention, there is provided a method of topically applying a pharmaceutical liquid to a patient using a device of the invention, wherein the method comprises: a) removing the closure means on the applicator tip; b) grasping the device in one hand by placing the index and middle finger on each of the flanges and a thumb on the cap; c) exerting pressure down on the cap to cause the penetrating tip to puncture the container seal to create an air communication between the through bore and the container, and permitting the inflow of air into the container resulting in dispensing of liquid through the applicator tip onto the patient; d) removing the exerted pressure from the cap so that the spring bias causes the penetrating tip to move in a direction away from the container seal and the seal on the valve stem bearing against the corresponding seal on the inner wall of the through bore to stop the air communication through the valve between the interior of the container and the external environment resulting in the stoppage of dispensing of liquid through the applicator tip onto the patient.

In an embodiment of the invention, there is provided a device for storing and dispensing a topical pharmaceutical liquid comprising: A) a substantially rigid elongated container, configured to hold the liquid therein, having a proximal end and a distal end with respective openings and a passage extending between the openings, the proximal end of the container having an external radial surface, the proximal opening being closed by a container seal and the distal end of the container tapering into an applicator tip, the distal opening being closed by a closure means; and B) an air valve comprising (a) a valve body having a top end and a bottom end, wherein the bottom end of the valve body comprises a container seal having a protrusion sticking out from the plane of the container seal; in the protrusion (52) is joined to the container seal by means of a hinge and a breakaway junction; and the the bottom end of the valve body and the proximal end of the container are sealed together to form an air tight container, wherein the valve body has peripheral flanges, wherein the top end of the valve body has a valve seat including an area defining a through bore extending from the top end to the bottom end of the valve body, wherein the through bore has an inner wall and has a seal protruding out along the circumference of said inner wall, wherein the valve seat includes a resilient engaging means, said engaging means projecting upwards from said valve seat; the valve seat further comprises a cylindrical collar projecting upwards from said valve seat along the periphery of the through bore opening and forming an extension of the through bore; and (b) a substantially rigid valve stem having a top end and a bottom end, wherein the stem is moveable within the through bore towards the top or bottom end of the through bore, the valve stem has a circumferential edge and has seal on said circumferential edge which can bear against a corresponding seal on the inner wall of the through bore; the valve stem further comprising a penetrating tip at bottom end of the stem for pushing against the protrusion sticking out from the plane of the container seal resulting in puncturing the container seal along the breakaway seal when the penetrating tip is moved towards the container seal to establish air communication through the valve between the interior of the container and the external environment; and a cap at the top end of the stem having a top and side wall, wherein the side wall has resilient engaging means for engaging the corresponding engaging means on the valve seat; wherein the valve has a spring for biasing the penetrating tip away from the container seal, wherein the valve has a configuration which is a stored position, an dispensed position or a sealed position; the stored position is when the valve is configured such that the container seal is not punctured by the penetrating tip; the dispensed position is when the valve is configured such that the penetrating tip punctured the container seal and the seals on the valve stem and the inner wall of the through bore do not create an air-tight seal, permitting air communication to be formed through the valve between the interior of the container and the external environment resulting in the liquid being dispensed from the container; and the sealed position is when the valve is configured such that the penetrating tip has moved away from the container and the seal on the valve stem bears against the corresponding seal on the inner wall of the through bore to create an air-tight seal prohibiting air communication to be formed through the valve between the interior of the container and the external environment resulting in no liquid being dispensed from the container; wherein the engaging means of the a cap and the valve seat are engaged with each other to hold the penetrating tip in position when the valve is in the stored or sealed position; and wherein the applicator tip has a proximal end near the distal end of the container and a distal end which is near the distal opening of the container having an annular recessed groove in the wall of the applicator; and wherein the closure means is a break-away tip integrally moulded with the distal end of the applicator tip at a breakaway junction situated in the recessed groove, so as to form an integral piece therewith, resulting in the break-away junction being recessed away from distal opening of the container.

In an embodiment of the invention, there is provided a device wherein the container seal comprises a protrusion joined to the container seal by means of a hinge and a breakaway junction, such that the break away junction breaks when the penetrating tip pushes down on the protrusion, and the hinge enables the protrusion to remain joined to the seal; establishing air communication where air can flow through the valve between the interior of the container and the external environment.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A device for storing and dispensing a topical pharmaceutical liquid comprising:
    a) a substantially rigid elongated container, configured to hold the liquid therein, having a proximal end and a distal end with respective openings and a passage extending between the openings, the proximal end of the container having an external radial surface, the proximal opening being closed by a container seal and the distal end of the container tapering into an applicator tip, the distal opening being closed by a closure means;
    b) an air valve comprising
        (i) a valve body having a top end and a bottom end, wherein the bottom end of the valve body and the proximal end of the container are sealed together, wherein the valve body has peripheral flanges, wherein the top end of the valve body has a valve seat including an area defining a through bore extending from the top end to the bottom end of the valve body, wherein the through bore has an inner wall and has a seal protruding out from said inner wall, wherein the valve seat includes a resilient engaging means, said engaging means projecting upwards from said valve seat and being of two different heights;
        the valve seat further comprises a cylindrical collar projecting upwards from said valve seat along the periphery of the through bore opening and forming an extension of the through bore;
        (ii) a substantially rigid valve stem having a top end and a bottom end, wherein the stem is moveable within the through bore towards the top or bottom end of the through bore, the valve stem has a circumferential edge and has a seal on said circumferential edge which can bear against a corresponding seal on the inner wall of the through bore;
        the valve stem further comprising a penetrating tip at the bottom end of the stem for puncturing the container seal when the penetrating tip is moved towards the container seal to establish air communication through the valve between the interior of the container and the external environment; and a cap at the top end of the stem having a top and side wall, wherein the side wall has resilient engaging means for engaging the corresponding engaging means on the valve seat;
    wherein the valve has a spring for biasing the penetrating tip away from the container seal,
    wherein the valve has a configuration which is a stored position, a dispensed position or a sealed position;
    the stored position is when the valve is configured such that the container seal is not punctured by the penetrating tip;
    the dispensed position is when the valve is configured such that the penetrating tip punctured the container seal and the seals on the valve stem and the inner wall of the through bore do not create an air-tight seal, permitting air communication to be formed through the valve between the interior of the container and the external environment resulting in the liquid being dispensed from the container; and
    the sealed position is when the valve is configured such that the penetrating tip has moved away from the container and the seal on the valve stem bears against the corresponding seal on the inner wall of the through bore to create an air-tight seal prohibiting air communication to be formed through the valve between the interior of the container and the external environment resulting in no liquid being dispensed from the container;
    wherein the engaging means of the cap and the valve seat are engaged with each other to hold the penetrating tip in position when the valve is in the stored or sealed position; and
    wherein the applicator tip has a proximal end near the distal end of the container and a distal end which is near the distal opening of the container having an annular recessed groove in the wall of the applicator; and
    wherein the closure means is a break-away tip integrally molded with the distal end of the applicator tip at a breakaway junction situated in the recessed groove, so as to form an integral piece therewith, resulting in the break-away junction being recessed away from distal opening of the container.

2. A method of topically applying a pharmaceutical liquid to a patient using a device according to claim 1, wherein the method comprises:
    a) removing the closure means on the applicator tip;
    b) grasping the device in one hand by placing the index and middle finger on each of the flanges and a thumb on the cap;

c) exerting pressure down on the cap to cause the penetrating tip to puncture the container seal to create an air communication between the through bore and the container, and permitting the inflow of air into the container resulting in dispensing of liquid through the applicator tip onto the patient;

d) removing the exerted pressure from the cap so that the spring bias causes the penetrating tip to move in a direction away from the container seal and the seal on the valve stem bearing against the corresponding seal on the inner wall of the through bore to stop the air communication through the valve between the interior of the container and the external environment resulting in the stoppage of dispensing of liquid through the applicator tip onto the patient.

* * * * *